United States Patent

Rose

[11] Patent Number: 6,083,191
[45] Date of Patent: Jul. 4, 2000

[54] ULTRASONIC SURGICAL APPARATUS

[75] Inventor: Emery S. Rose, New York, N.Y.

[73] Assignee: Sherwood Services AG, Schaffhausen, Switzerland

[21] Appl. No.: 08/116,261

[22] Filed: Aug. 9, 1993

Related U.S. Application Data

[63] Continuation of application No. 07/832,534, Feb. 7, 1992, abandoned.

[51] Int. Cl.[7] .................................................. A61B 17/36
[52] U.S. Cl. ............................................ 604/22; 606/169
[58] Field of Search ................................ 310/316; 604/22; 606/169

[56] References Cited

U.S. PATENT DOCUMENTS

| | | |
|---|---|---|
| 3,589,363 | 6/1971 | Banko et al. . |
| 3,967,143 | 6/1976 | Watanabe et al. . |
| 4,012,647 | 3/1977 | Balamuth et al. . |
| 4,056,761 | 11/1977 | Jacoby et al. . |
| 4,063,557 | 12/1977 | Wuchinich et al. . |
| 4,223,676 | 9/1980 | Wuchinich et al. . |
| 4,425,115 | 1/1984 | Wuchinich . |
| 4,750,488 | 6/1988 | Wuchinich et al. . |
| 4,750,902 | 6/1988 | Wuchinich et al. . |
| 4,827,911 | 5/1989 | Broadwin et al. . |
| 4,888,514 | 12/1989 | Takahashi et al. ....................... 310/316 |
| 4,922,902 | 5/1990 | Wuchinich et al. ........................ 604/22 |
| 4,931,047 | 6/1990 | Broadwin et al. ......................... 604/22 |
| 4,965,532 | 10/1990 | Sakurai ........................................ 331/4 |
| 4,979,952 | 12/1990 | Kubota et al. . |
| 5,015,227 | 5/1991 | Broadwin et al. ......................... 604/22 |
| 5,113,116 | 5/1992 | Wilson ...................................... 310/316 |
| 5,116,343 | 5/1992 | Ams et al. ................................ 606/128 |
| 5,151,085 | 9/1992 | Sakurai et al. ............................. 604/22 |

FOREIGN PATENT DOCUMENTS

| | | |
|---|---|---|
| 0394583 | 10/1990 | European Pat. Off. . |
| 4000947 | 10/1990 | Germany . |
| 2211369 | 6/1989 | United Kingdom . |

Primary Examiner—David H. Willse

[57] ABSTRACT

An electrical apparatus for driving an ultrasonic piezoelectric crystal transducer in a surgical handpiece for the fragmentation and aspiration of tissue, which apparatus includes an electronic control loop in combination with a voltage source amplifier having an output which is connected to the piezoelectric crystal transducer with a tuning inductor in parallel. A control system for monitoring the control loop and a component for controlling tissue selectivity are also disclosed.

5 Claims, 5 Drawing Sheets

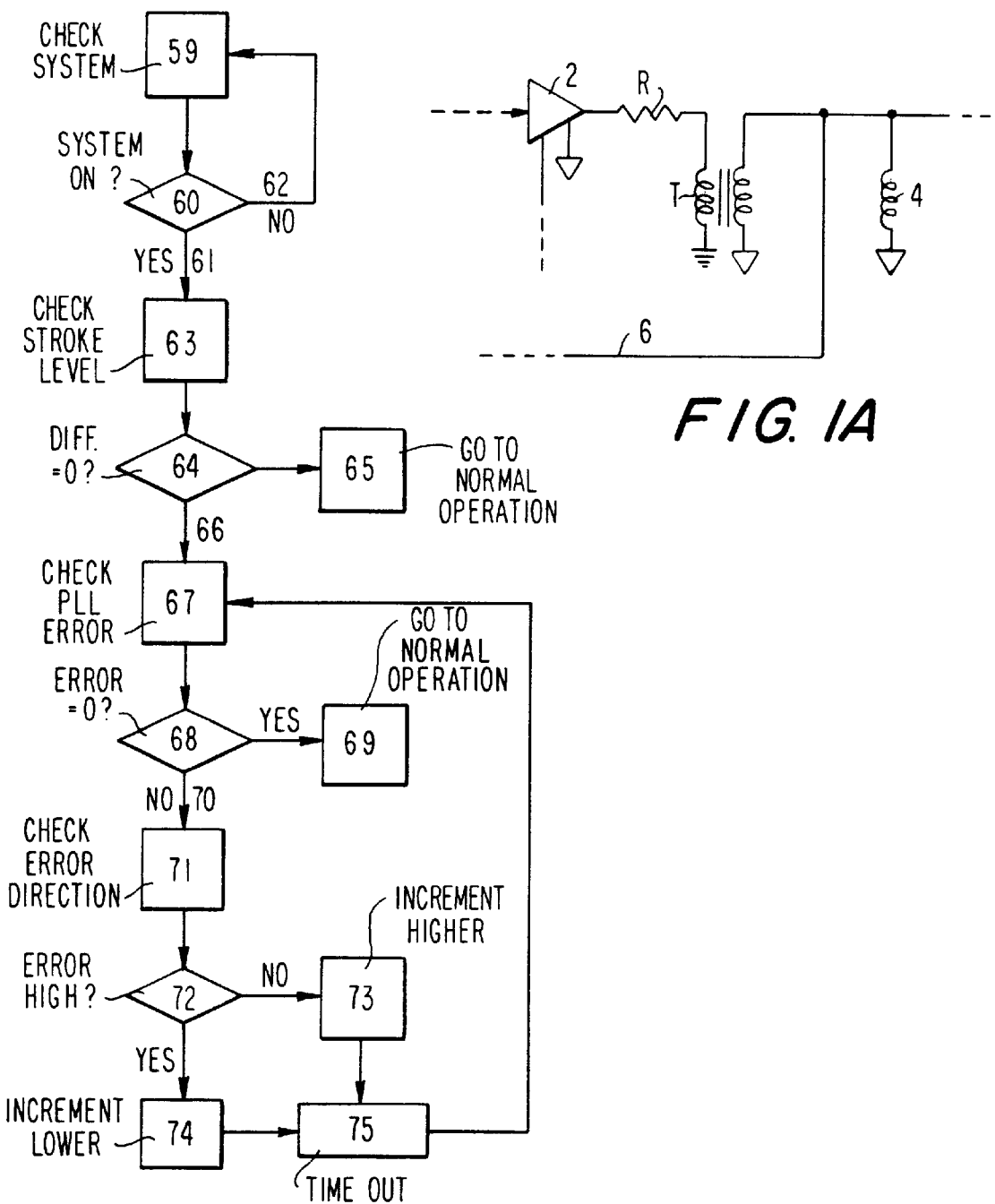

ULTRASONIC SURGICAL APPARATUS

This is a continuation of application Ser. No. 07/832,534, filed on Feb. 07, 1992, now abandoned.

BACKGROUND OF THE INVENTION

The present invention relates to an electrical apparatus for driving an ultrasonic transducer in a surgical handpiece for the fragmentation and aspiration of tissue at an operation site on a patient, and to electronic control loops in the electrical circuitry of the apparatus. In particular, the invention relates to an apparatus for driving an ultrasonic surgical device while maintaining the vibration frequency at mechanical resonance utilizing a feedback control. The invention is also concerned with means for controlling amplitude and with a digital interface for monitoring performance and restoring normal operation when the system parameters exceed analog control loop boundaries. The invention also provides means for controlling the tissue selectivity of the apparatus.

The use of ultrasonically vibrating surgical devices for fragmenting and removing unwanted tissue by aspiration with precision and safety has led to the development of valuable surgical procedures. Initially, the technique of surgical aspiration was applied to the fragmentation and removal of cataract tissue as disclosed, for example, in U.S. Pat. No. 3,589,363. Later, similar techniques were applied with significant success to neurosurgery and other surgery specialties where the application of ultrasonic energy through a handheld device for selectivity removing tissue on a layer-by-layer basis with precise control was found to be feasible.

Certain devices known in the art characteristically produce continuous vibrations having a substantially constant amplitude at a frequency of about twenty to about thirty KHz up to about forty to about fifty KHz. U.S. Pat. Nos. 4,063,557, 4,223,676 and 4,425,115 disclose a device suitable for the removal of soft tissue which is particularly adapted for removing highly compliant elastic tissue mixed with blood. Such a device is adapted to be continuously operated when the surgeon wishes to fragment and remove tissue, and generally is operated by a foot switch.

A known instrument for the ultrasonic fragmentation of tissue at an operation site and aspiration of the tissue particles and fluid away from the site is the CUSA model System 200 Ultrasonic Aspirator manufactured and sold by Valleylab, Inc. of Stamford, Conn.; see also U.S. Pat. No. 4,827,911. When the longitudinally vibrating tip in such an aspirator is brought into contact with tissue it gently, selectively and precisely fragments and removes the tissue. Advantages of this unique surgical instrument include little damage to healthy tissue in a tumor removal procedure, blood vessels can be skeletonized, healing of tissue is promoted, no charring or tearing of margins of surrounding tissue, only minimal pulling of healthy tissue is experienced, and excellent tactile feedback for selectively controlled tissue fragmentation and removal is provided.

In many surgical procedures where ultrasonic fragmentation instruments are employed additional instruments are required for tissue cutting and hemostasis at the operation site. For example, hemostasis is needed in desiccation techniques for deep coagulation to dry out large volumes of tissue and also in fulguration techniques for spray coagulation to dry out the surface of tissues.

The apparatus disclosed in U.S. Pat. Nos. 4,931,047 and 5,015,227 provides hemostasis in combination with an ultrasonically vibrating surgical fragmentation instrument and aspirator. The apparatus effectively provides both a coagulation capability and an enhanced ability to fragment and aspirate tissue in a manner which reduces trauma to surrounding tissue.

U.S. Pat. No. 4,750,488 and its two continuation U.S. Pat. Nos. 4,750,902 and 4,922,902 disclose a method and apparatus which utilize a combination of ultrasonic fragmentation, aspiration and cauterization.

In an apparatus which fragments tissue by the ultrasonic vibration of a tool tip, it is desirable, for optimum efficiency and energy utilization, that the transducer which provides the ultrasonic vibration should operate at resonant frequency. When the transducer is a piezoelectric crystal the frequency at which it vibrates will correspond to the frequency of the electrical driving signal which causes the vibration. The operation is most efficient when the transducer vibrates at its resonant frequency. However, changes in operational parameters, such as, changes in temperature, thermal expansion and load impedance, result in deviations in the resonant frequency.

Accordingly, controlled changes in the frequency of the driving signal are required to track the resonant frequency.

The circuit disclosed in U.S. Pat. No. 4,750,488 includes a frequency control loop which depends upon a feedback signal obtained by adding two signals that are proportional to the voltage and current input to the piezoelectric transducer.

U.S. Pat. No. 4,965,532 discloses a circuit for driving an ultrasonic transducer including a frequency control means utilizing a feedback control dependent upon first and second phase detection signals.

It has now been found that an efficient frequency control is obtained with the aid of a unique control loop which includes a feedback piezoelectric crystal mechanically coupled to the piezoelectric transducer.

The use of a feedback crystal in a tuned circuit which provides a filtered signal to control a driving signal in an ultrasonic system is disclosed in U.S. Pat. No. 4,012,647. The system disclosed in this patent is not a surgical apparatus and the combination of ultrasonic vibrator, amplifier and tuning inductance with feedback from the feedback crystal to the input of the amplifier, constitutes an oscillator. In contrast thereto, the novel circuit of the present invention incorporates a voltage controlled oscillator (VCO) as part of a control loop. The feedback signal from a feedback crystal is input to the control loop which then drives the amplifier. The advantage of this novel circuit is that it tracks mechanical resonance without electrical interaction.

A problem which frequently arises during the operation of an ultrasonic surgical apparatus which includes a feedback control loop is the propensity of the control loop to lock into an unwanted adjacent frequency rather than the desired resonant frequency.

The occurrence of this problem depends upon the frequency spectrum of the system and the control loop characteristics. If the control loop is underdamped the large transient overshoots upon start-up or rapidly changing loads move the driving frequency toward the adjacent frequencies. The propensity of the control loop to lock into an unwanted adjacent frequency increases with the magnitude of control loop overshoot and the proximity of said adjacent frequencies.

Due to performance requirements and manufacturing variances, it is difficult to produce a pure analog control system which is not prone to said irregularities. Also, a difficulty in the manufacture of ultrasonic vibrators is the variation in resonant frequency due to variations in materials and manufacturing processes. Such variations in resonant frequency result in a greater magnitude of error signal in the operation of the control loop. The probability of irregularities increases in direct proportion to the magnitude of the error signal.

It has now been found that such irregularities may be avoided by the use of a microprocessor-based system interactively coupled to an analog control loop, which system provides a digital interface for monitoring performance and restoring normal operation when the system parameters exceed analog control loop boundaries.

SUMMARY OF THE INVENTION

In accordance with the present invention there is provided an electrical apparatus for driving an ultrasonic piezoelectric crystal transducer in a surgical handpiece for the fragmentation and aspiration of tissue, which apparatus comprises voltage controlled oscillator in series with an amplifier and a first electronic control loop connected from a feedback piezoelectric crystal through a phase comparator and a loop filter to the voltage controlled oscillator, which feedback crystal is mechanically coupled to said transducer and provides a feedback signal which is a function of the actual frequency of vibration of the transducer and which phase comparator compares the phase of the feedback signal and of the driving signal and provides a control signal which maintains the driving signal at the resonant frequency of the transducer, wherein said amplifier is a voltage source amplifier having an output which is connected to the piezoelectric crystal transducer with a tuning inductor in parallel.

Preferably the handpiece incorporates a piezoelectric crystal transducer operatively connected to a tool having a distal tip, which transducer, upon activation by an electrical driving signal provided by the apparatus according to the invention, ultrasonically vibrates said tool tip so that the tip is capable of fragmenting tissue at a surgical operation site, and aspiration means for removing fragmented tissue from said site.

The piezoelectric crystal transducer is connected in parallel to a tuning inductor to form a network having a resonant frequency corresponding to the operational frequency of the transducer and optimizing the coupling of the voltage source amplifier to a real load. A piezoelectric crystal is a voltage controlled device and, consequently, the advantage of a voltage source amplifier in parallel with a tuning inductor is that it provides a more direct control of the piezoelectric driven vibrator. Also, in a preferred embodiment, a low value resistor is connected in series on the output of the voltage source amplifier for added stability. This preferred embodiment is a substantial improvement over the conventional use of a series tuning inductor, since the response is instant because there is no inductive phase lag.

The invention also provides an apparatus as described above which includes a second control loop comprising means for sensing the amplitude of vibration of the transducer and providing an amplitude signal, means for comparing the amplitude signal with a command signal adjustable by an operator and means for maintaining the vibration at a desired operational amplitude under varying loads by adjusting the driving signal as required to bring the amplitude level into conformity with the command signal level.

Preferably, the second control loop includes a converter which converts the RMS AC feedback signal to DC.

The invention further provides a control system for monitoring one or more electronic control loops to detect and respond to error conditions occurring during operations controlled by said loop or loops, which system comprises a microprocessor coupled to an analog-to-digital converter and a multiplexer, wherein the output from each control loop is input to the multiplexer, the output from the multiplexer is converted to digital form in the converter to provide an input digital signal which is processed in the microprocessor to respond with an appropriate algorithm to correct the error condition.

The above described control system is particularly adapted for monitoring a frequency control loop such as the above-described first control loop included in an apparatus according to the invention, or for monitoring an amplitude gain control loop such as the second control loop included in an apparatus according to the invention, or, in the most preferred embodiment, for monitoring both first and second control loops. This preferred embodiment is more particularly described hereinafter with reference to FIG. 1 of the accompanying drawings.

The invention still further provides an apparatus as described above which includes means for achieving tissue selectivity in an ultrasonic surgical aspirator comprising a limiter connected to the output of the amplitude gain control loop whereby the maximum error signal output by the loop may be adjusted and limited by an operator.

Thus, a preferred handpiece comprises a piezoelectric crystal transducer which is operatively connected to a tool having a distal tip, which transducer, upon activation by an electrical driving signal, ultrasonically vibrates the tool tip so that the tip is capable of fragmenting tissue at a surgical site, a feedback piezoelectric crystal mechanically coupled to the transducer, and aspiration means for removing fragmented tissue from the surgical site. Preferably, the transducer and feedback crystal are mounted within an electrically insulated housing and switching means for selecting and actuating the various operations are mounted on the housing so that the handpiece may be hand-operated.

BRIEF DESCRIPTION OF THE DRAWINGS

The invention will be more particularly described with reference to the accompanying drawings, in which:

FIG. 1A is a portion of a modified circuit between points A—A on FIG. 1;

FIG. 3 is an algorithm which illustrates the steps for checking phase lock loop error and making necessary adjustments to bring said error to zero;

DETAILED DESCRIPTION OF THE INVENTION

Figure 1:
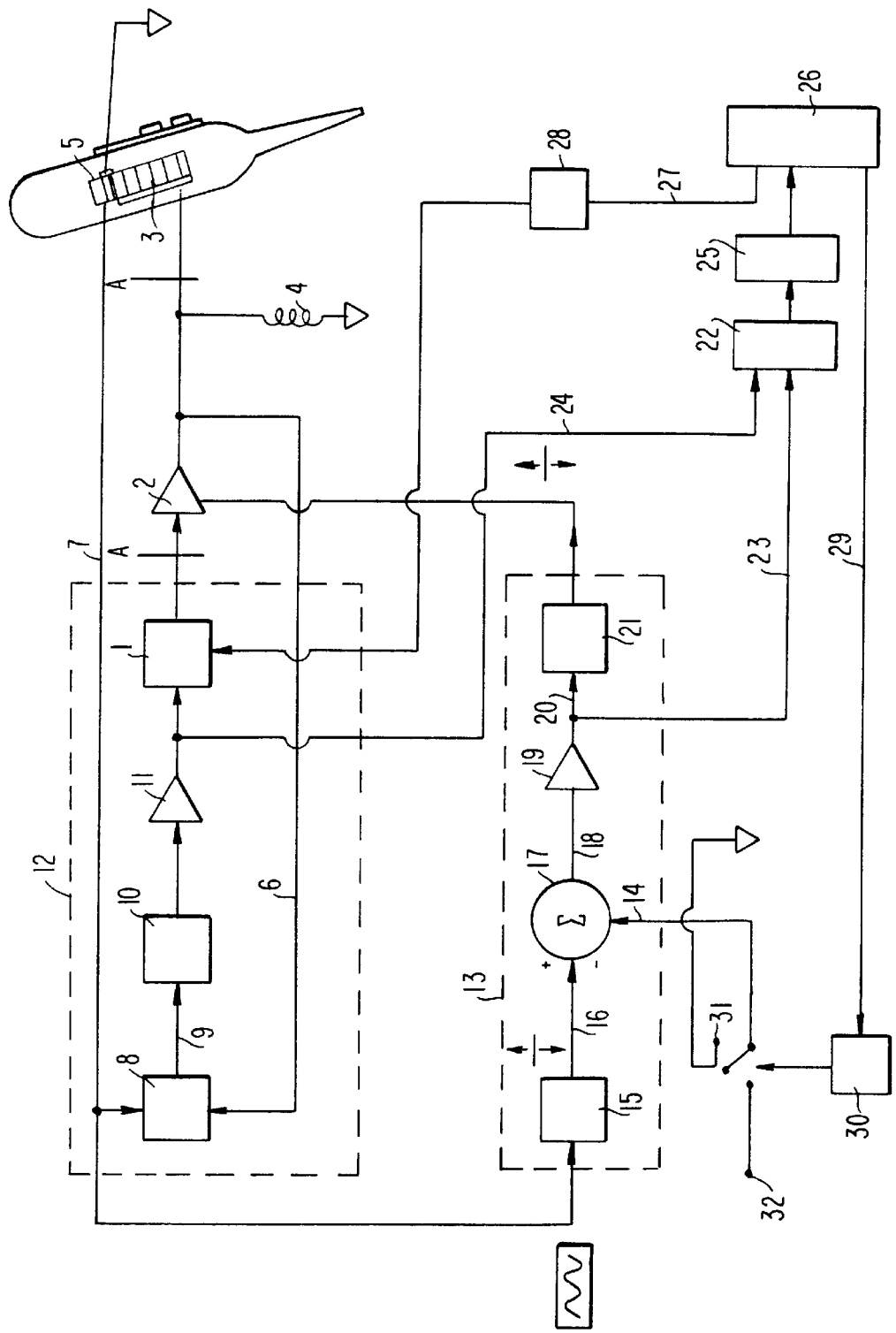
FIG. 1 is a schematic representation of control loops according to one embodiment of the invention.

The apparatus illustrated in FIG. 1 of the drawings comprises a voltage controlled oscillator (VCO) 1 which drives, through a power amplifier 2, a driving piezoelectric crystal 3 with a sinusoidally oscillating voltage. This voltage is imparted to the drive crystal at the output of a voltage source power amplifier 2, with a parallel inductor 4 and optionally with an impedance matching transformer T (FIG. 1A). Also, for stability, a low value resistor R is connected to the output of the amplifier (FIG. 1A). The frequency of the oscillation at the output of the VCO is determined by the voltage imparted to the input of the VCO. The midpoint of the oscillator's frequency range should be set at the point where it is anticipated that the system will normally be running and the range of the frequency should cover the range over which the system will vary in normal use.

The piezoelectric drive crystal 3 responds to the sinusoidally oscillating voltage applied to it by the VCO by vibrating at the same frequency and causing the entire ultrasonic vibrator assembly to vibrate at such frequency.

The feedback crystal 5, being in the ultrasonic assembly, vibrates with it. When stress is applied to a piezoelectric crystal, the crystal responds by developing a proportional voltage. This voltage is an indication of how the assembly is vibrating. The amount of deflection of the vibrating assembly is indicated by the level of voltage across the feedback crystal. If the vibrating assembly is vibrating at a given sinusoidal frequency, the voltage signal from the feedback crystal will be a sine wave of such frequency. The resonant frequency of oscillation of the vibrating assembly is the frequency at which the minimum amount of power is required to drive it. This frequency is indicated by a 90 degree phase displacement between the sine wave of the driving signal and the sine wave of the feedback signal.

The two signals, drive 6 and feedback 7, are imparted to the inputs of a phase comparator 8. The output 9 of the phase comparator gives the cosine of the phase angle between the drive and feedback sine wave signals.

If the resonant frequency is the same as the center frequency of the VCO, the VCO will drive the drive crystal at its resonant frequency. The phase angle fed back to the phase comparator between drive and feedback will be 90 degrees giving 0 (zero) volts to the VCO, through a loop filter 10 and an amplifier 11 which is described hereinafter; and the VCO will continue to drive the vibrating assembly at its resonant frequency.

If the resonance suddenly changes, due to loading, the phase angle between the two waves will no longer be 90 degrees. The output of the phase comparator will be the cosine of something other than 90 degrees, which will no longer be zero. When this is felt by the VCO (the output of the phase comparator is fed to the VCO through a gain amplifier 11), the VCO will shift its output frequency in proportion to the gain of the amplifier multiplied by the signal from the phase comparator and in a sense so as to bring the phase angle between the drive and feedback signals back to 90 degrees. As the phase angle moves back toward 90 degrees the cosine of the phase angle moves back toward zero. The system will be in equilibrium when the phase angle is as close to 90 degrees as possible with a voltage level applied to the VCO sufficient to maintain oscillation at a frequency different from its center frequency to correspond to the new resonant frequency. The more gain in the amplifier, the less will be the error.

Further complication exists due to the fact that the vibrating mechanical system has an inertia which impedes the rate at which its vibration frequency or amplitude may be changed. A sudden load on the tip of the vibrator can change its resonance. The phase comparator 8 will respond by applying a correcting voltage through the amplifier 11 to the VCO. If the gain of the amplifier is excessive, the VCO will attempt to change the driving frequency much faster than the vibrating mechanical assembly can respond. By the time the vibrating mechanical assembly reaches the proper frequency defining resonance, the VCO will have overshot it by some amount. The loop then attempts to correct in the opposite direction and once again overshoots, and so on. If the system is stable, the overshoot decreases on each cycle and eventually settles. If the system is unstable, the overshoot does not decrease on each cycle but either stays constant and oscillates or else increases on each cycle until the system locks into an adjacent frequency or is damaged.

The loop consisting of the phase comparator 8, its output 9, the gain amplifier 11 and the VCO 1 comprises a phase locked loop (PLL) defined schematically by dashed lines 12.

A second control loop 13 is provided for controlling amplitude. This is the automatic gain control loop (AGC). The operator sets the amplitude of oscillation required for the vibrating tip at the command input 14. The sine wave 7 returning from the feedback crystal is converted to a D.C. level as a function of its amplitude by the RMS-to-DC converter 15. This signal 16 is then fed to a summing node 17, the output 18 of which is the error signal between the feedback and the command input 14, which error signal is fed to an error amplifier 19. The error amplifier 19 transmits a signal at its output in proportion to the difference between the two inputs to the summing node 17. A signal 20 controls the amplitude of the drive signal which is the output of the power amplifier 2 which drives the driving piezoelectric crystal 3. The system is in equilibrium when the least amount of difference exists between the two inputs, 14 and 16, but enough difference exists to achieve a level at 20 to drive the crystal and feedback a signal from the feedback crystal to achieve this minimal difference between 14 and 16. Error decreases with gain, but safe gain margins must be maintained to avoid instability.

One feature of ultrasonic aspirators is the selectivity with which specific types of tissue may be fragmented and aspirated with little or no effect on adjacent tissue of other specific types. In some surgical procedures this is a desirable effect, while in others it is desirable to have a less selective fragmentation capability.

It has been found that a greater or lesser tissue selectivity may be achieved by varying, through a limiter 21, the maximum amplitude of the driving signal applied by the AGC. The limiter 21 is connected to the amplitude gain control loop whereby the maximum error signal output by the loop may be adjusted and limited by an operator.

A multiplexer 22 has as its inputs an error signal 23 from the automatic gain control loop (AGC), 13, and an error signal 24 from the PLL. The output from the multiplexer is fed to an analog-to-digital converter 25, the output of which is transmitted to a microprocessor ($\mu$P) 26. An output signal 27 from the microprocessor is transmitted to a center frequency adjusting unit 28, the output of which is fed to the VCO 1. A second output signal 29 from the microprocessor is transmitted to a switching unit 30 for switching the command input between either zero or a low reference point 31 and an operator amplitude set point 32.

Figure 2:
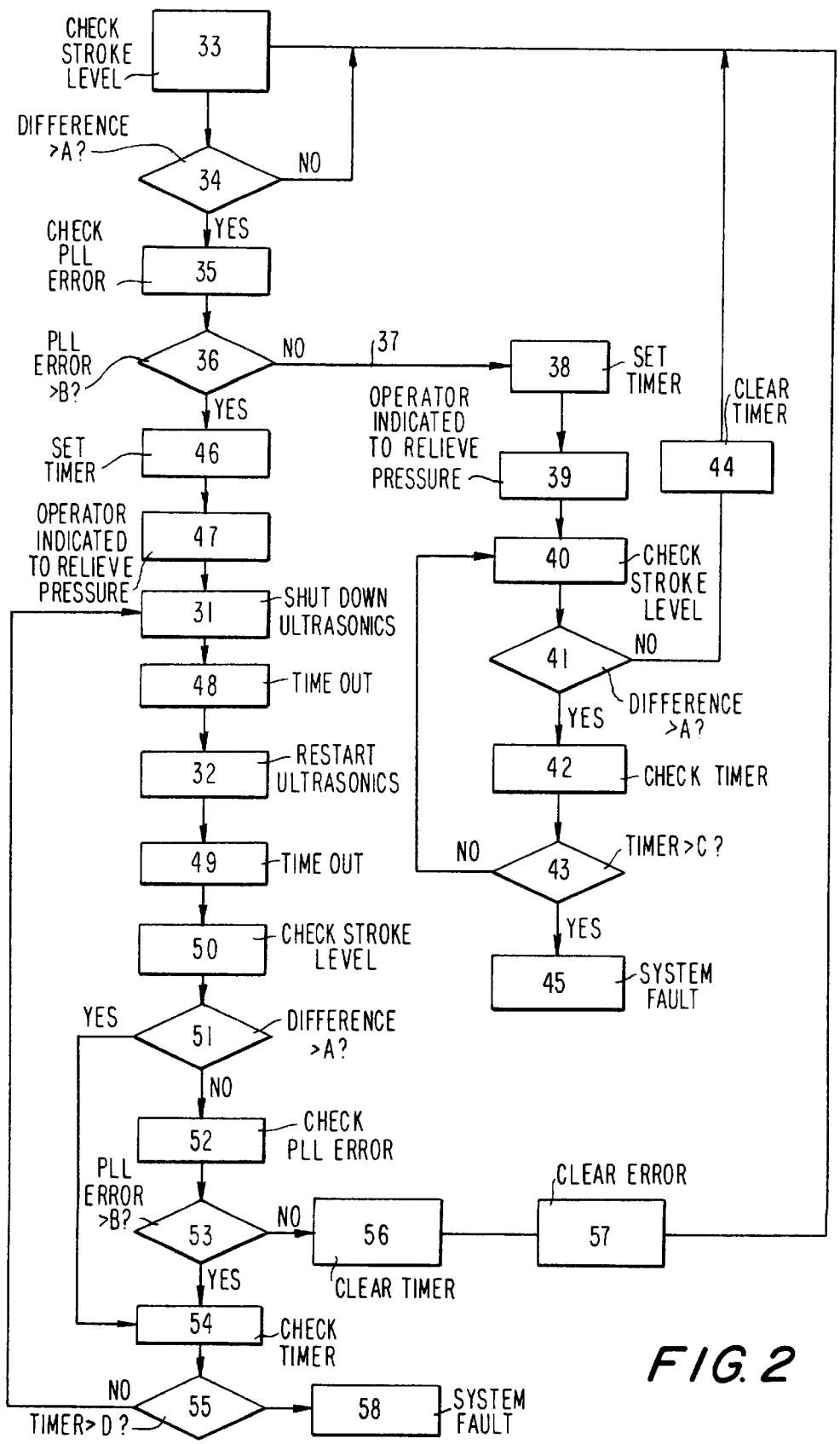
FIG. 2 is an algorithm illustrating the steps for monitoring performance and restoring normal operation when the system parameters exceed analog control loop boundaries.
Figure 4:
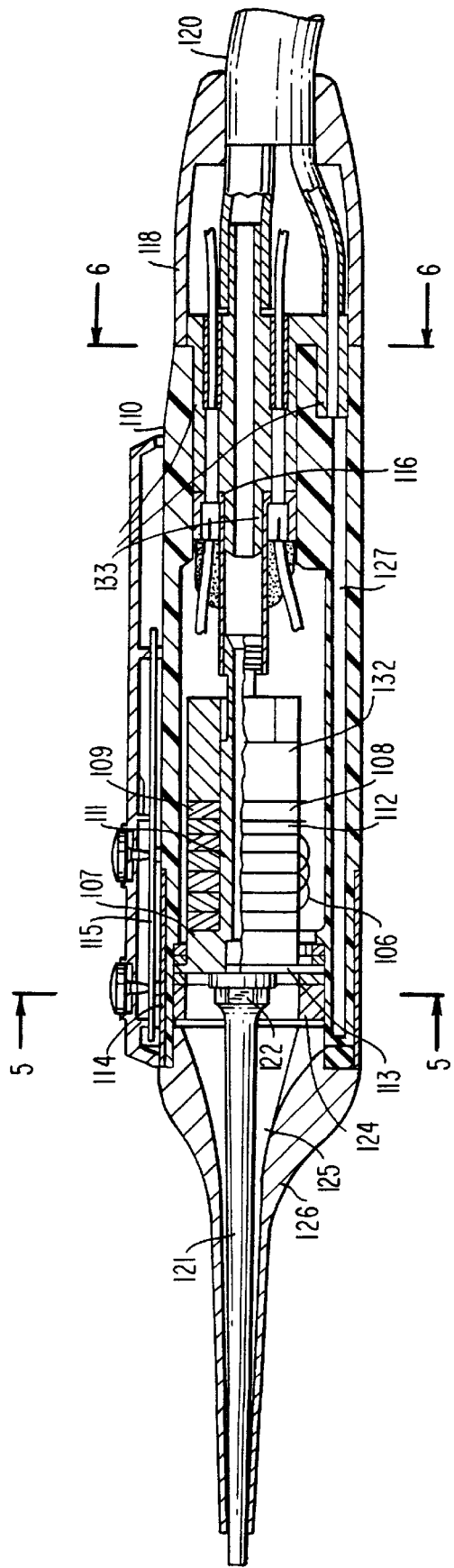
FIG. 4 is a side elevation, partly in section, of a preferred handpiece used with the apparatus of the invention.
Figure 6:
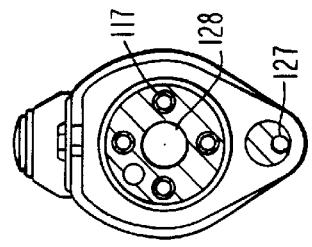
FIG. 6 is a rear view through line 6—6 of FIG. 4.
Figure 5:
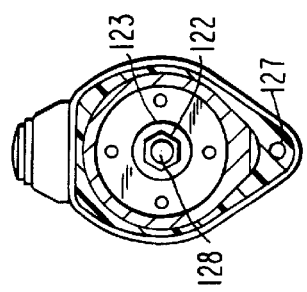
FIG. 5 is a front view section through line 5—5 of FIG. 4.
Figure 7:
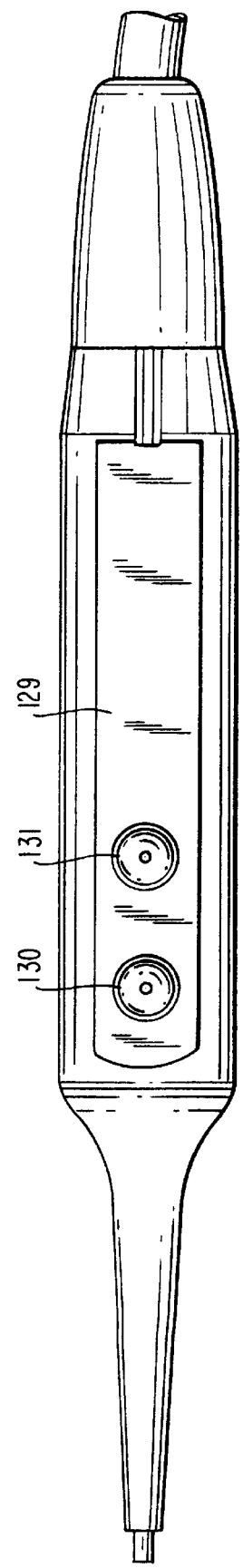
FIG. 7 is a top view of the handpiece.

The system in normal operation is given by the algorithm in FIG. 2. The AGC lop error signal 20 is polled and the level is checked 33. A difference 34 greater than a predetermined value (>A) indicates a stall condition A stall condition is such that the amplitude of vibration is substantially lower than the commanded input 14 so indicating excessive loading, control loop lockup on an adjacent unwanted frequency, or some other error condition. If a stall condition is not indicated the polling 33, 34 will continue and the PLL is allowed to operate normally. If a stall condition is indicated, the PLL error is checked 35. An abnormally high PLL error 36 (>B) indicates a lockup on an unwanted adjacent frequency.

If the PLL error is not greater 37 than the predetermined value (>B), and the stall condition is indicated, the following algorithm is executed: A timer 38 in the microprocessor system 26 is set for a maximum allowable period of time for correction.

The interaction of the microprocessor system in this portion of the algorithm is an indication 39 to the operator by means of an appropriate audible, visual, tactile or other communication means, that excessive pressure is being applied to the ultrasonic surgical handpiece. The microprocessor will continue to poll 40, 41 for relief of the pressure and for an indication of excessive time by means of the timer 42, 43. Upon relief of the stall condition, the microprocessor clears the timer 44 and then clears means for operator communication 44 and returns to polling 33, 34. If the stall is not cleared and the check timer 42 indicates that the time limit has been exceeded 43 the system will shut down 45 disallowing further operation and an error condition will be signaled to the operator by the communication means 45. A condition where both loop errors 34, 36 are simultaneously in excess of the predetermined values is an indication that the system has locked into an unwanted adjacent resonance. One way of correcting this condition is to relieve all pressure from the ultrasonic surgical device 46, set the timer 47, and switch the commanded input for the AGC loop to zero 31.

Vibration is stopped by applying zero volts 31 through switch 30 to the command input 14 of the AGC loop. Ample time 48 is allowed for the ultrasonic generator to dissipate all stored energy 48. The command input is restored through switch 30 to the operator set level 32. Ample time is allowed for the ultrasonic generator to achieve steady state vibration amplitude level 49. The error levels are rechecked 50, 51, 52, 53 along with the timer 54. If error condition persists 51, the timer is checked 54. The algorithm will repeat continuously until either the error conditions are relieved or the timer value is exceeded 55. If the error conditions 50, 51, 52, 53 are relieved prior to the timer value 55 being exceeded, the timer is cleared 56, and the algorithm 57 (see FIG. 3) adjusts the PLL center frequency. The PLL error correcting algorithm is executed, the communication means and timer are cleared 56 and the ultrasonic generator is returned to normal operation. If the timer value is exceeded 55, the ultrasonic generator is disabled 58 and an error message is communicated to the operator by means of the above-described communication means 58.

The operation schematically represented by 57 in FIG. 2 may be defined by the algorithm illustrated in FIG. 3. The start of the algorithm is a polling 59, 60 to determine whether vibration has been activated 61 or not 62. At the start of vibration, the difference between the operator adjusted commanded input for stroke level and the actual stroke level is determined by the level of the AGC loop error signal 63. If the signal is not zero 64, a loaded vibration condition is indicated causing the algorithm to go to normal operation 65. If the signal is zero 66, the PLL error signal is checked 67 to determine if zero error exists 67. If zero error exists 68, the algorithm goes to normal operation 69. If the error is not zero 70, a determination of the direction of the error is made 71, 72 and an increment of adjustment is imparted to the VCO in the appropriate direction, either higher 73 or lower 74. A loop settling time is allowed 75 (timeout) and the error is once again checked 67. This is repeated until the error is zeroed 68 after which the system is returned to normal operation 69.

The handpiece illustrated in FIGS. 4–7 of the accompanying drawings comprises a housing 110, which is preferably made of an electrically insulating plastic material. The housing accommodates a piezoelectric crystal transducer comprising a stack of toroidal piezoelectric crystals 111. Each crystal is mechanically coupled to each adjacent crystal and each crystal is energized with alternating electrical energy by opposite polarity electrodes on either side of each crystal. Common polarity electrodes 106 are formed as a single part so as to reduce the number of wires within the handpiece. At the rear of the transducer is a feedback piezoelectric crystal 112 which is mechanically coupled to the driving crystals of the transducer and is commonly grounded with the driving crystals. The feedback crystal also has a projecting electrode connected to an electrical line (not shown) for conveying the feedback signal to an electrical contact at the rear of the housing and thence, through a connector, to a control circuit. The entire piezoelectric assembly, including the driving and feedback crystals, is electrically insulated from the front driver 107 and the rear driver 132 by insulating ceramic elements 108 and an insulating sleeve 109. The driving crystals, feedback crystal and associated electrodes are electrically insulated on both the inside and outside with a polymeric coating to prevent dielectric breakdown across the crystals and across the insulating ceramic elements 108.

The transducer also has a projecting electrode 133 connected to an electrical line (not shown) for conveying high frequency electrical energy to the front driver 107 for the purpose of tissue dissection or desiccation.

The front end of the transducer terminates in a toroidal flange 113 which is mounted in a rubber mount 114 bearing against the inner wall of the housing and a steel washer 115. The rear end of the transducer is attached through a vibration isolation joint to a contact plate 116 which is hermetically bonded into the housing 110.

Electrical lines from the piezoelectric driving crystals and feedback crystal terminate in electrical contacts 117 (FIG. 6) at the rear end of the housing. The electrical contacts operatively engages with complementary sockets in a connector 118 when the connector is connected to the housing. The electrical lines are connected to a generator and control circuit through a cable 120 attached to the rear end of the connector. The connector O-rings 133 isolate irrigation liquid, aspiration liquid and any liquid external to the handpiece from each other as well as from the electrical contacts. The connector 118 when connected to the handpiece simultaneously engages the ultrasonic power and feedback lines, the electrosurgery active wire, the aspiration tube and the irrigation tube. This the handpiece may be sterilized independent of any cabling.

Attached to the front end of the transducer is a hollow tool 121 having a distal tip which is capable of fragmenting tissue when the tool is ultrasonically vibrated by the transducer. The proximal end of the tool is threaded and a hexagonal periphery 122 adjacent the proximal end enables the tool to be threadably engaged to a cooperating thread in a front plate attached to a flange 113 at the front end of the transducer. A washer 124 around the front plate bears against a rubber mount 114 so that the combination of mount plates and washers forms a liquid-tight seal about the front end of the transducer. This seal is essential to prevent any irrigation liquid from entering the part of the housing which contains the transducer and the electrical components associated therewith.

Irrigation liquid, usually saline solution, is conveyed to the tool tip through a channel 125 formed between the inner wall of a flue 126 and the outer wall of the tool 121. The irrigation liquid reaches the channel 125 from a conduit 127 passing along the lower part of the housing, which conduit is supplied from an external reservoir through a tube (not shown) terminating in the connector 118.

The tool 121 is hollow to allow fragmented tissue to be aspirated from the operation site. Aspiration is normally conducted by suction through the hollow tool and through a tube 128 (FIG. 5 and FIG. 6) passing axially through the housing and out through the connector.

Since the irrigation liquid, which may be conductive, may have the electrical potential of the high frequency energy applied to the front driver, sufficient insulation distance is required for operator safety at the detachable connection points. Thus, a flue 126 is designed to shroud the housing 110 for a regulatory required insulation tracking distance. Likewise, the connector 118 also may shroud the housing 110 to achieve the required insulation tracking distance.

In the embodiment illustrated in the drawings the handpiece is hand operated and a switch module 129 is mounted on the housing. The illustrated module contains two switches which are electrically connected to a circuit board within the housing for operating the handpiece. It is to be understood that a handpiece used in the apparatus of the invention may have more than two hand switches or may be operated by a foot switch.

I claim:

1. An electrical apparatus and an ultrasonic piezoelectric crystal transducer in a surgical handpiece for the fragmentation and aspiration of tissue the ultrasonic piezoelectric crystal transducer driven by the apparatus, which apparatus comprises:

a voltage controlled oscillator in series with an amplifier and a first electronic control loop connected from a feedback piezoelectric crystal through a phase comparator and a loop filter to the voltage controlled oscillator, which feedback crystal is mechanically coupled to an ultrasonic piezoelectric crystal transducer in a surgical handpiece and the feedback piezoelectric crystal provides a feedback signal which is a function of the actual frequency of vibration of the ultrasonic piezoelectric crystal transducer in a surgical handpiece and which phase comparator compares the phase of the feedback signal of the feedback piezoelectric crystal and of a driving signal and provides a control signal which maintains the driving signal at the resonant frequency of the ultrasonic piezoelectric crystal transducer in a surgical handpiece, wherein said amplifier is a sinusoidally oscillating voltage source amplifier, the sinusoidally oscillating voltage source amplifier in parallel with a tuning inductor and having an output which is connected to the ultrasonic piezoelectric crystal transducer in a surgical handpiece and to provide the driving signal, includes a second control loop comprising:

a means for sensing the amplitude of vibration of the ultrasonic piezoelectric crystal transducer in a surgical handpiece and providing an amplitude signal in proportion thereto, means for comparing the amplitude signal with a command signal adjustable by an operator and generating an error signal in proportion to the difference between the amplitude signal and the command signal, the error signal of the second control loop changing the amplitude of vibration to a desired level with the second control loop as an automatic gain control loop, the amplitude signal in proportion with the command signal under varying loads and in which the automatic gain control loop including a limiter so the maximum error signal output of the loop may be adjusted and limited by an operator to achieve tissue selectivity, and a switching unit connected to provide a feedback command signal as input to the second control loop, the switching unit connects to limit selectivity with the operator amplitude set point or a low reference point according to second output signal.

2. An apparatus according to claim 1, in which the piezoelectric crystal transducer is operatively connected to a tool having a distal tip, which transducer, upon activation by a driving signal, ultrasonically vibrates the tool tip so that the tip is capable of fragmenting tissue at a surgical operation site.

3. An apparatus according to claim 2, in which the handpiece includes aspiration means for removing fragmented tissue from said surgical site.

4. An apparatus according to claim 1, in which a low value resistor is connected in series on the output of the voltage source amplifier for added stability.

5. An apparatus according to claim 1, in which the second control loop includes a converter which converts the RMS AC feedback signal to DC.

* * * * *